United States Patent [19]

Urushizaki et al.

[11] Patent Number: 5,298,393
[45] Date of Patent: Mar. 29, 1994

[54] MONOCLONAL ANTIBODY FOR HUMAN ACID-GLUTATHIONE S-TRANSFERASE AND PROCESS FOR PREPARATION THEREOF

[75] Inventors: Ichiro Urushizaki; Yoshiro Niitsu; Hiroshi Maruyama, all of Sapporo; Hideaki Suzuki, Koganei; Kenji Hosoda, Kawagoe; Hitomi Honda; Yasuhiko Masuho, both of Hino, all of Japan

[73] Assignee: Teijin Limited, Osaka, Japan

[21] Appl. No.: 759,808

[22] PCT Filed: Nov. 19, 1986

[86] PCT No.: PCT/JP86/00592
§ 371 Date: Jul. 21, 1987
§ 102(e) Date: Jul. 21, 1987

[87] PCT Pub. No.: WO87/03377
PCT Pub. Date: Jun. 4, 1987

Related U.S. Application Data

[63] Continuation of Ser. No. 86,129, Jul. 21, 1987, abandoned.

[30] Foreign Application Priority Data

Nov. 21, 1985 [JP] Japan .................. 60-259858

[51] Int. Cl.$^5$ .......................................... G01N 33/53
[52] U.S. Cl. .................................. 435/7.1; 435/7.4; 435/7.92; 435/7.94; 530/387.1; 436/548
[58] Field of Search .......... 435/7.1, 7.4, 7.92, 435/7.94, 810; 530/387, 806; 436/548, 518, 808; 935/96, 110

[56] References Cited

U.S. PATENT DOCUMENTS 4,486,530 12/1984 David et al. .................. 435/7

OTHER PUBLICATIONS

Köhler, et al., *Nature* vol. 256, "Continuous Cultures of Fused Cells Secreting Antibody of Predefined Specificity", pp. 495–497, Aug. 7, 1975.
Maruyama et al., *The Journal of Biological Chemistry*, vol. 259, No. 20, Oct. 25, 1984, 12444–12448, "Distinctions between the Multiple Cationic Forms of Rat Liver Glutathione S-transferase".
Wang et al., Different Forms of Ya Subunit of Ligandin and Glutathione S-Transferase B Detected by Monoclonal Antibodies, Mar. 1, 1985, Federation Proceedings, vol. 44, No. 3, p. 861.
Chemical Abstracts, vol. 100, No. 11, Mar. 12, 1984 p. 406, Abstract No. 83937t.

*Primary Examiner*—Robert J. Hill, Jr.
*Assistant Examiner*—Laurie Scheiner
*Attorney, Agent, or Firm*—Sughrue, Mion, Zinn, Macpeak & Seas

[57] ABSTRACT

A monoclonal antibody for human acid glutathion S-transferase. This monoclonal antibody can be utilized as a diagnostic for cancers such as cancer of liver, gastric cancer, and cancer of the blood.

12 Claims, 1 Drawing Sheet

MONOCLONAL ANTIBODY FOR HUMAN ACID-GLUTATHIONE S-TRANSFERASE AND PROCESS FOR PREPARATION THEREOF This application is a continuation application of application Ser. No. 07/086,129, filed Jul. 21, 1987, now abandoned.

TECHNICAL FIELD

The present invention relates to a monoclonal antibody which recognizes glutathione S-transferase (hereinafter abbreviated as GST) that can be used as the diagnostic reagent for carcinomas such as cancer of the liver, stomach cancer, etc. and a process for preparing it.

BACKGROUND OF THE ART

GST is known as a detoxicating enzyme which catalyzes the conjugation (reaction) of various substances, which enter into an organism, or analogous substances (hereinafter referred to as substrates) which are produced in vivo, with glutathione of reduced type. Many of the substrates react with the in vivo protein or nucleic acid to cause a change to a morbid state (for instance, carcinogenesis) but the reactivity of these substrates are neutralized by said conjugation to be transformed into more water-soluble products and metabolized in the liver, etc. and finally excreted out of the body.

GST is found existing in various kinds of living species inclusive of mammals and is especially contained in considerable quantities in the liver, spleen, kidney, lung, brain, skeletal muscles, placenta, and small intestine, and also found in the skin, red blood cell, and white blood corpuscule though very small in amount. GST generally comprises various types of enzymes and is not only specific to species but also specific to the internal organs and tissues.

In the case of a human being, basic GST and acid GST are known (see The Journal of Biological Chemistry, vol. 259, No. 20, pp. 12,444-12,448 and pp. 12,449-12,455 (1984)). Basic GST has the isoelectric point (pI) of 7-9 and consists of two subunits, each subunit having a molecular weight of about 23,000. Acid GST has the isoelectric point (pI) of 4-5 and consists of two subunits, each subunit having a molecular weight of about 22,000. Basic GST exists mainly in the liver of a healthy normal adult and also in other places such as kidney, testicle, small intestine, brain, and lung though less in amount. While acid GST scarcely exists in the liver of a healthy normal adult but found existing in the liver of a newborn baby, placenta, such proliferous cells as liver cancer cells, stomach cancer cells, etc., red blood cell, and white blood corpuscule. Since acid GST produced by the proliferous cells is extricated out of the site of its production into the blood, it has possibilities of being utilized as a tumor marker highly specific to such digestive system cancers as liver cancer, stomach cancer, colon cancer, esophagus cancer, and cancer of the pancreas, and such blood tumors as cancer of the blood and lymphocytoma.

DISCLOSURE OF THE INVENTION

The present inventors have conducted an intensive research to obtain a monoclonal antibody which can detect the aforementioned tumor marker with high accuracy and finally prefected the present invention.

This invention is concerned with monoclonal antibody which recognizes human acid GST. Though it is naturally presumed that human acid GST somewhat differs from each other in structure depending upon the internal organ or tissue where it is produced, it is acid GST produced from the liver of a newborn baby, placenta, red blood cell, and proliferous cells such as liver cancer cell and stomach cancer cell that are useful as the marker to be used for the diagnosis of cancer. Therefore, a monoclonal antibody which recognizes such acid GST in common (for instance, which recognizes common subunits) should desirably be used in the present invention, and more particularly a mouse antibody of IgG type is desirable. Also, the monoclonal antibody of the present invention has a characteristic property that it does not exhibit a cross reaction with human basic GST.

The present invention also includes a method for determing acid GST with the use of the aforementioned monoclonal antibody and a kit of reagents to be used such determination.

BEST MODE OF CARRYING OUT THE INVENTION

Figure 1:
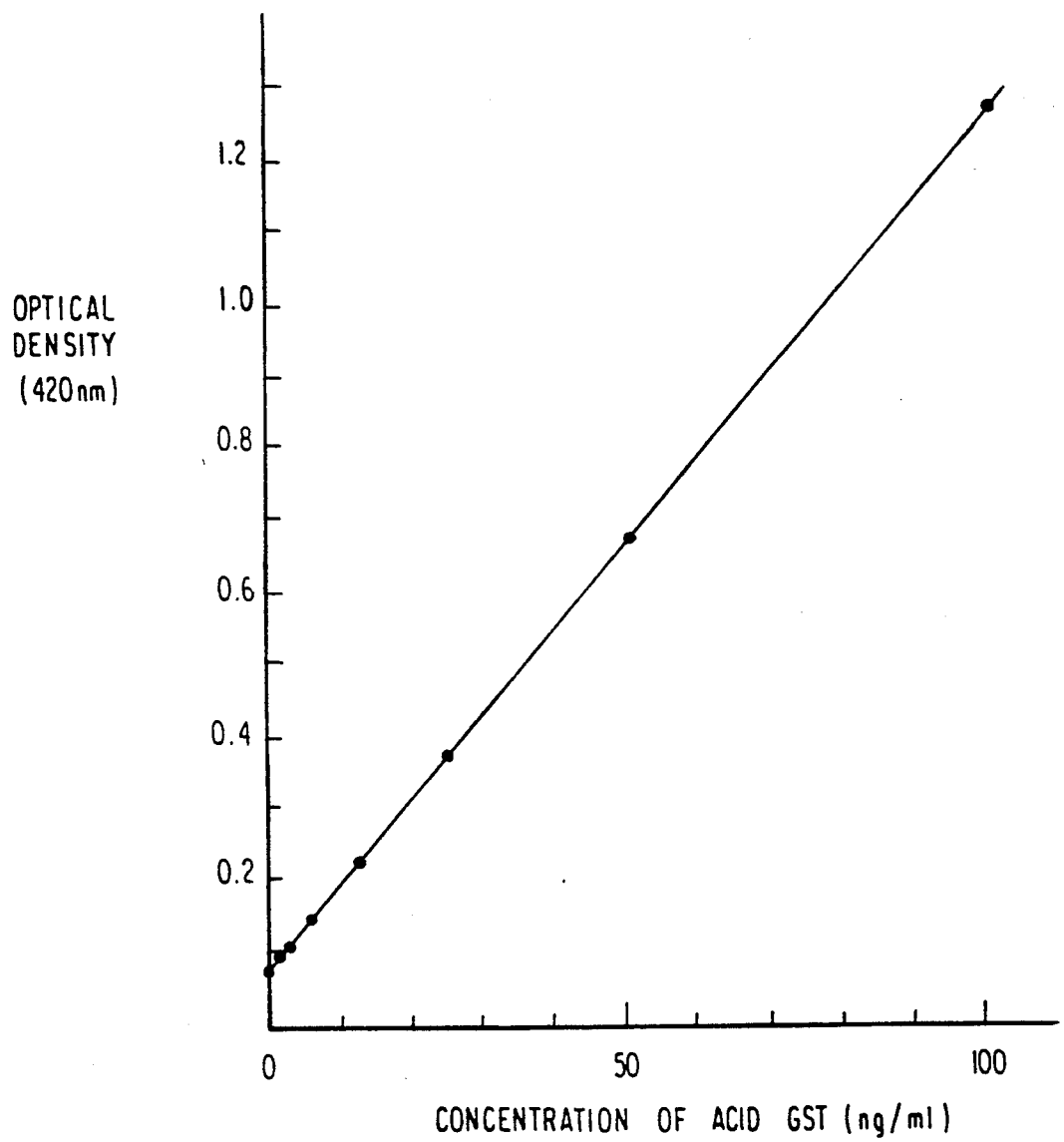
FIG. 1 is a drawing to show the relation between the concentration of acid GST and the optical density (420 nm).

The monoclonal antibody of this invention can be obtained first by obtaining a hybridoma, which produce monoclonal antibody that recognize acid GST, by fusing a myeloma cell with an antibody producible cell of an animal immunized desirably with human acid GST, then by culturing thus obtained hybridoma and/or a cell line arising therefrom, and finally collecting monoclonal antibody specific to human acid GST from the culture.

The human acid GST of this invention is made up of two subunits, each subunit having a molecular weight of about 22,000, forms a single band in the sodium dodecyl sulfate polyacrylamide gel electrophoresis (SDS-PAGE), and has the isoelectric point (pI) of 4-5. Various isozymes are included in the human acid GST of this invention so far as they satisfy these conditions.

A hybridoma producible of a monoclonal antibody which recognizes human acid GST can be produced according to the method of cell fusion which is publicly known per se. The method comprises firstly immunizing animals such as a monkey, equine, bovine, goet, sheep, rabbit, rat, mouse, etc. with human acid GST, then collecting antibody-producing cells (lymph corpuscles) from their spleen, lymph node, etc., and lastly fusing there cells with human or animal myeloma cells. As the myeloma cells, mouse myeloma cells can be used conveniently and they include P3-X63-Ag8, P3-X63-Ag8-U1, P3-NS1/1-Ag4-1, P3-X63-Ag8-6.5.3, SP2/0-Ag14, F0, and MPC11-45.6TG1.7 of BALB/C mice.

The following conditions are, for instance, required for carrying out the cell fusion. Antibody-producing cells and myeloma cells are mixed at a ratio of 10:1 to 1:10, preferably 1:1 to 1:3 and a properly prepared cell fusion solution, for instance, comprising about 35% polyethylene glycol (molecular weight approx. 1,000 to 6,000) and RPMI 1640 containing 7.5% dimethyl sulfoxide, is added thereto, and the mixture is stirred at room temperature to 37° C. for 1 to several minutes. The mixture is then diluted slowly with RPMI 1640 containing 10% fetal calf serum and after having been washed, the dilution is adjusted with a HAT (lypoxanthineaminopterin-thymidine) selective liquid culture medium to have a cell concentration of 1 to $5 \times 10^5$/ml. Thus adjusted liquid culture medium was placed in a 96-well plate in 0.2 ml portions and cultured in 5% $CO_2$ air at 35°-38° C. for 2-3 weeks. In the HAT liquid culture medium, only hybridomas can survive and 8-azaguanine resistant myeloma cells and myeloma/-myeloma fused cells can not survive (antibody-producible cells which are not fused perish in a course of few days). From the colonies of hybridomas, only those that secrete monoclonal antibody specific to human acid GST are selected. This selecting procedure (screening) can be performed by enzyme-linked-immunosorbent assay (ELISA) to check whether monoclonal antibodies produced by the respective hybridomas cause an antigen-antibody reaction with acid GST. Hybridomas which secrete the desired monoclonal antibody must then be made into cloned cells by cloning. This procedure can be conducted concretely by limiting dilution. About 2 to 3 weeks later, colonies grown in the 96-well plate are picked up and again have their antibody activity against human acid GST examined by ELISA. The selected hybridomas are cultured to produce the desired monoclonal antibodies specific to acid GST.

Another method for obtaining a monoclonal antibody is one in which antibody-producing cells are infected with Epstein-Barr virus (hereinafter abbreviated as E-B virus) to produce transformed cells, and thus produced cells and/or cell line arising therefrom are cultured, and monoclonal antibodies which have a nature to bind to human acid GST are collected from the culture.

E-B virus is regarded as a virus causative of Burkitt's lymphoma and nasopharyngeal carcinoma, belonging to the herpesvirus group. After having been infected with E-B virus, antibody producing cells are cultured in a 5% $CO_2$ incubator for about 2 to 3 weeks to form transformed cells consisting of many heterogenous colonies. Then out of these transformed cells, only those that secrete monoclonal antibodies specific to acid GST are selected by the aforementioned method. By following the same procedure as mentioned above, transformed cells which have been cloned can be obtained.

In the present invention, the screened hybridomas or transformed cells are thereafter cultured to make them produce the desired specific monoclonal antibody. The hybridomas or transformed cells, which have been selected by cloning and are producible of antibodies which recognize human acid GST, can be kept in frozen storage and mass cultured by an appropriate method after such storage. And a monoclonal antibody, which specifically bind to acid GST, can be obtained from the culture supernatant. In another method, these cells are transplanted to an animal to cause a tumor and the desired antibodies can be obtained from the ascitic fluid and serum of the animal. Purification of the monoclonal antibody of this invention is performed by affinity chromatography with the use of protein A.

The monoclonal antibody of the present invention which binds to human acid GST can be used first of all for determining acid GST which functions as a tumor marker for the diagnosis of cancer of digestive organ, etc., also for making an internal diagnosis by imaging conducted by means of tissue cloloring of the tissue affected by cancer cells or by means of radioactive labelling, and further for curing cancerous diseases in combination with anti-cancer agents.

As the method for measuring human acid GST with the use of a monoclonal antibody for human acid GST of this invention, there are a sandwich method wherein an antibody fixed to an insoluble support (hereinafter referred to as an "immobilized antibody") and a labelled antibody are made to react with human acid GST and thus produced sandwich complex is detected by a labelled substance, and a competitive method wherein labelled human acid GST and human acid GST in the sample are made to react competitively with the antibodies are determine the human acid GST in the sample from the quantity of the labelled antibodies reacted with the antibodies, thus making it possible to determine the human acid GST in the sample in both methods.

In the measurement of acid GST by the sandwich method, a choice may be made between the 2-step method and the 1-step method or simultaneous assay method: the former method comprises making the immobilized antibody react with acid GST firstly, removing non-reacting substances with careful washing, and adding labelled antibody thereto to obtain a triformed sandwich complex of immobilized antibody-human acid GST-labelled antibody, and the latter method in which immobilized antibody, labelled antibody, and human acid GST are mixed simultaneously to react with each other, thus forming a sandwich complex in a single process.

As the insoluble support which is used in the measurement of acid GST in the present invention, such synthetic resins as polystyrene, polyethylene, polypropylene, polyvinyl chloride, polyester, polyacrylic ester, nylon, polyacetal, and fluororesin, such polysaccharides as cellulose and agarose, glass and metal may be mentioned.

To speak of the form of an insoluble support, supports of various forms, for instance, such as tray, sphere, fiber, stick, plate, vessel, cell, and test tube may be used.

As for the labelling materials, it is advantageous to use an enzyme, fluorescent substance, luminous substance, and radioactive substance. As the enzyme, peroxidase, alkaline phosphatase, and $\beta$-D-galactosidase; as the fluorescent substance, fluorescein isothiocyanate and phycobilliprotein; as the luminous substance, isoluminol and lucigenin; and as the radioactive substance, $^{125}I$, $^{131}I$, $^{14}C$, and $^3H$ may be used respectively; however, besides these exemplified in the above, any other materials may also be used so far as they are usable in the immunological measurement method.

In case where an enzyme is used as the labelling agent, a substrate or a color former, as case may require, to determine its activity.

When peroxidase is used as the enzyme, $H_2O_2$ can be used as the substrate, and 2,2'-azino-di-[3-ethylbenzthiazoline sulfonate (b)] ammonium salt (ABTS), 5-amino salicylic acid, 0-phenylenediamin, 4-aminoantipyrine, and 3,3', 5,5'-tetramethylbenzine are used as the color former. When alkaline phosphatase is used as the enzyme, 0-nitrophenylphosphate is used as the substrate, and when $\beta$-D-galactosidase is used as the enzyme, fluorescein-di-($\beta$-D-galactopyranoside) and 4-methylumbelliferyl-$\beta$-D-galactopyranoside can be used as the substrate.

The present invention also involves a kit consisting of the aforementioned antibodies and reagents in its scope. A desirable example is a kit of reagents for measuring human acid GST existing in the body fluid such as serum by the immunological method, mainly consisting of (1) immobilized antibody which recognizes human acid GST, (2) labelled antibody which recognizes human acid GST but binds to an antigen component different from the immobilized antibody, and (3) reagents for detecting said labelled antibody, as case may require, as main constituents and besides these reagents, such known reagents as dissolving agents, cleaning agents, and reaction terminators may further be added as the constituents, if necessary.

The following Examples illustrate the invention.

EXAMPLE 1

(1) Isolation and purification of acid GST

The human placenta was cut into small pieces in 0.25 M sucrose and 10 mM phosphate buffer (pH 7.4) and homogenized in a homogenizer. The obtained homogenate was centrifuged at 10,000 $\times$g at 4° C. for 30 minutes and the supernatant was collected. Then this supernatant was further centrifuged at 100,00 $\times$g at 4° C. for 1 hour and the resulting supernatant was collected. This supernatant was dialyzed against 10 mM phosphate buffer (pH 6.8) and the dialyzate was applied to a column of CM cellulose which had been pre-equilibrated with the same buffer and non-adsorbed fractions were collected. The collected and pooled fraction was injected into the column filled with Sepharose fixed with reduced glutathione to adsorb acid GST. Thereafter the column was washed with 10 mM phosphate buffer (pH 7.4) and when the absorption intensity at 280 nm is the ultraviolet absorption spectrum of the elluence became 0.02 or lower, reduced glutathione-containing Tris buffer (pH 8.0) was made to pass through the column to have the adsorbate eluted. After this eluate was ultrafiltered, the filtrate was subjected to gel filtration by Sephadex G 100 (Pharmacia) column chromatography with the use of 10 mM phosphate buffered saline solution (PBS) (pH 7.4) to obtain fractions containing acid GST. These fractions were again ultra-filtered to be concentrated and this concentrate was subjected to the column isoelectric point electrophoresis (pH 3.5–10) by use of an isoelectric point electrophoresis column (LKB) by using sucrose for making the concentration gradient and using ampholyne (Pharmacia: pH 3.5–10) for making the pH gradient, thus obtaining fractions which contained purified acid GST.

(2) Preparation of antibody

Acid GST, which had been obtained from the human placenta by extraction as described in the above, was emulsified into complete Freund's adjuvant and was intraperitoneally given to 7-week old BALB/C mice in a dose of 100 mg/mouse. Fifteen days after the priming dose was given, a booster dose was given to the mice in the same way as the first one. Ten days later, an inspection was made to confirm the increase of antibodies in the blood, and 7 days after the confirmation was made, a dose of antigen was further given intravenously in an amount of 100 mg/mouse.

On the other hand, myeloma cells P3-X63-Ag8-U1 had been kept cultured in RPMI 1640 (Gibco) containing 15% fetal calf serum. Three days after the final immunization, the spleen cells collected from the mice and P3U1 were fused by use of polyethylene glycol 4000 according to the method of Oi et al. (Selective Methods in Cellular Immunology, 1980, pp. 351–372) and added to 96-well microplates. After the cell fusion, the culture medium was replaced with RPMI medium containing 100 $\mu$M hypoxanthine, 0.4 $\mu$M aminopterin, and 16 $\mu$M thymidine (HAT medium). In 2 to 3 weeks of culture in HAT medium, only hybridoma resulting from the fusion of a spleen cell with a myeloma cell remained growing. The antibody activity in the liquid culture medium of hybridoma was examined by ELISA mentioned below.

(3) Screening of antibody

Acid GST was fixed to the plates for ELISA and subjected to the blocking in a liquid containing 10 mM phosphate saline solution (pH 7.4) and 3% (W/V) bovine serum albumin (BSA). After the blocking was over, 50 ml of the liquid culture medium of hybridoma was added to ELISA plates and left standing at room temperature for 2 hours. After the liquid culture medium of hybridoma was removed, the plates were washed, 100 ml of peroxidase-labelled goat anti-mouse IgG-Fc specific antibody (2 mg/ml) was added thereto, and was made to undergo a reaction at 37° C. for 1.5 hours. After the removal of this enzyme-labelled antibody liquid and washing, 200 ml of 0.1M citrate buffer (pH 4.6) containing 0.05% 2,2'-azino-di-[3-ethylbenzthiazoline sulfonate (6)] (ABTS) and 0.0034% $H_2O_2$ was added for staining to detect the antibodies.

(4) Cloning and preparation of monoclonal antibody

The selection of the liquid culture medium of hybridoma which produces an antibody specific to acid GST and the cloning by limiting dilution were performed, thus finally obtaining 4 kinds of hybridomas of single clone type. These respective hybridomas were intraperitoneally administered to BALB/C mice which had been given pristane to effect proliferation and obtained abdominal dropsy containing monoclonal antibodies. The antibodies were precipitated by adding 50% saturated ammonium sulfate to the obtained abdominal dropsy and the precipitate was dissolved in 0.1 M phosphate saline solution (pH 8.0). After the solution was dialyzed, the dialyzate was subjected to protein A-Sepharose CL4B column (Pharmacia) and the antibodies were eluted with 0.2 M glycine-hydrochlorine buffer (pH 3.0), followed by neutralization and purification.

The 4 monoclonal antibodies obtained from the respective hybridomas were named 2F, 5F, 2H, and 6A.

(5) Properties of monoclonal antibodies

The 4 kinds of monoclonal antibodies recognized GST arising from human fetus in the western blotting method which is explained hereinafter. Also it was made apparent by the inhibition assay, in which acid GST fixed to ELISA plates was made to react with the biotin-labelled first antibody and the coexisting non-labelled second antibody, that all of the 4 kinds of monoclonal antibodies recognize each other's different epitope (antigenetic determinant) since all the combinations of two kinds of antibodies showed no change in the reacting amount of the biotin-labelled antibodies.

These antibodies reacted with neither human basic GST nor serum of a normal healthy person.

(6) Western blotting technique

Antigen specific to monoclonal antibody was fixed by western blotting technique, or a method proposed by Towbing et al. (Pro. N.A.S. 76, pp. 4,350–4,354).

Firstly, human fetus acid GST was subjected to SDS-PAGE, after which protein in the slab gel was transferred to nitrocellulose sheet under the conditions of electrolytic solution buffer of 25 mM glycine and 20% (V/V) methanol, voltage gradient of 7 V/cm, and 2 hours. Each lane of the nitrocellulose sheet was cut off and one had its protein stained with Amido Black and the other one was subjected to enzyme immunoassay following the procedure mentioned below.

After the blocking performed by use of 3% (W/V) BSA-PBS, monoclonal antibody (2F or 5F) was added as the primary antibody. Thereafter, the addition of peroxidase-labelled goat antimouse IgG-Fc specific antibody as the secondary antibody, followed by washing and color-producing by addition of a substrate solution consisting of 0.04% 3,3'-diaminobenzidine, 0.0034% $H_2O_2$, and 0.01 M PBS, completed the detection and fixation.

EXAMPLE 2

Determination of acid GST (1) Thoroughly washed polystyrene beads (diameter 6 mm) were left in a PBS (pH 7.4) solution containing monoclonal antibody 2H at a concentration of 20 mg/ml at a temperature of 4° C. overnight, then washed with PBS, and subjected to the postcoating treatment by being left in 0.5% BSA aqueous solution at 4° C. overnight, thus obtaining monoclonal antibody fixed beads.

(2) Preparation of horseradish peroxidase-labelled monoclonal antibody

Fifty $\mu$l of a dimethylformamide solution containing N-(m-maleimide benzoate)-N-succinimide ester (MBS) at a concentration of 10 mg/ml added to 1.0 $\mu$l of a PBS solution of monoclonal antibody 6A (1.0 mg/ml) and the mixture was made to undergo a reaction at 25° C. for 30 minutes. The reaction mixture was then subjected to gel filtration on a Sephadex G-25 column with the use of 0.1 M phosphate buffer (pH 6.0) to have maleimidized monoclonal antibody and non-reacted MBS separated.

Besides the abovementioned procedure, 200 $\mu$l an ethanol solution of N-succinimidyl-3-(2pyridylthio) propionate (SPDP) at a concentration of 10 mg/ml was added to 1.0 $\mu$l of a 8.0 mg/ml PBS solution of horseradish peroxidase (HRP) and the mixture was made to undergo a reaction at 25° C. for 30 minutes. The reaction mixture was then purified by gel filtration on a column filled with Sephadex G-25 by use of 0.01 M acetate buffer (pH 4.5) and fractions containing pyridyldisulphidized HRP were collected and concentrated to one-tenth of its original volume in a collodion membrane bag on the ice bath. Thereafter, 1 ml of 0.1 M acetate buffer (pH 4.5) containing 0.85% NaCl and 0.1 M dithiothreitol was added thereto and the mixture was stirred at 25° C. for 30 minutes to reduce the pyridyldisulfide group which had been introduced into HRP molecules. The reaction mixture was then subjected to gel filtration on Sephadex G-25 column to obtain fractions containing thiolated HRP.

Thereafter, maleimidized monoclonal antibody and thiolated HRP were mixed together and concentrated in the collodion membrane bag on the ice bath to 4 mg/ml protein concentration and left standing at 4° C. overnight. The concentrate was then subjected to gel filtration on a column filled with ultragel Ac $A_{44}$ (LKB) to obtain HRP-labelled monoclonal antibody.

(3) Method for measuring acid GST by indirect sandwich enzyme immunoassay

Test tube incubation was performed at 37° C. for 4 hours by use of test tubes, each containing a piece of bead with monoclonal antibody 2H fixed thereto, 200 $\mu$l of 0.5% BSA-containing PBS solution (pH 7.4) which contained purified acid GST (standard substance) in the range of 1.0 $\mu$g/ml to 100 $\mu$g/ml, and 2 $\mu$l of 0.5% BSA-containing PBS solution (pH 7.4) which contained HRP-labelled monoclonal antibody 6A. Thereafter, each test tube had its solution content removed by suction, was washed with PBS, and then had 0.5 ml of 0.1 M phosphate-citrate buffer (pH 4.5) containing 0.05% 2,2'-azino-di-[3-ethylbenzthiazoline sulfonate (6)] ammonium salt (ABTS) and 0.003% hydrogen peroxide added thereto. After the incubation at 37° C. for 30 minutes, the enzyme reaction was stopped by adding 1 ml of 0.2 M oxalic acid aqueous solution as a reaction terminator to each tube.

The absorption intensity of this solution at the wavelength of 420 nm was measured with a spectrophotometer and plotted against the concentration of the standard substance to give a satisfactorily concentration-dependent calibration curve. The result is shown in FIG. 1.

(4) Determination of acid GST in clinical subject

Sera were collected from a normal healthy person and a patient with colon cancer and 50 $\mu$l of the respective sera were put in the test tubes separately. Each serum was diluted with 150 $\mu$l of 0.5% BSA-containing PBS solution (pH 7.4). Then a piece of bead fixed with monoclonal antibody 2 H and 200 $\mu$l of 0.5% BSA-containing PBS solution (pH 7.4) containing HRP-labelled monoclonal antibody 6 A were added to the respective test tubes and were incubated at 37° C. for 4 hours. Then the same procedures, inclusive of washing, enzyme reaction, and termination of the reaction, as those taken in the preparation of the aforementioned calibration curve were again carried out to measure the absorbance intensity at 420 nm with a spectrophotometer and the concentrations were obtained by use of the calibration curve. The result showed that the concentration of acid GST in the serum of the normal healthy person was 0.7 ng/ml and the concentration of acid GST in the serum of the patient with colon cancer was 35.0 ng/ml.

We claim:

1. A monoclonal antibody that specifically binds to human acid glutathione S-transferase.

2. The monoclonal antibody according to claim 1, wherein said human acid glutathione S-transferase is produced by proliferous cells.

3. The monoclonal antibody according to claim 1, wherein said monoclonal antibody is a mouse IgG monoclonal antibody.

4. The monoclonal antibody according to claim 1, wherein said monoclonal antibody recognizes acid glutathione S-transferase of human placental origin.

5. A method for measuring human acid glutathione S-transferase in a sample comprising the steps of:
   (a) reacting a monoclonal antibody that specifically binds to human acid glutathione S-transferase with a sample;
   (b) quantifying the amount of said reacted monoclonal antibody from step (a); and
   (c) calculating said human acid glutathione S-transferase from said quantified amount from said (b) in said sample.

6. The method for measuring human acid glutathione S-transferase according to claim 5, wherein said reacting step (a) further comprises the use of a first monoclonal antibody that specifically binds to human acid glutathione S-transferase and a second monoclonal antibody that specifically binds to human acid glutathione S-transferase, wherein said first monoclonal antibody is bound to a support and said second monoclonal antibody is labelled.

7. The method for measuring human acid glutathione S-transferase according to claim 6, wherein said second monoclonal antibody is labeled using a member selected from the group consisting of enzymes, fluorescent substances, luminous substances, and radioactive substances.

8. A reagent kit comprising:
   (1) a first monoclonal antibody that specifically binds to human acid glutathione S-transferase bound to a support,
   (2) a second monoclonal antibody that specifically binds to human acid glutathione S-transferase that binds to an epitope different from the first monoclonal antibody where said second monoclonal antibody is labeled, and
   (3) reagents for detecting said second antibody.

9. A method for diagnosing cancer which is accompanied by the presence of acid glutathione S-transferase in blood by measuring human acid glutathione S-transferase in a sample comprising the steps of:

(a) reacting a monoclonal antibody that specifically binds to human acid glutathione S-transferase with a sample;
   (b) quantifying the amount of said reacted monoclonal antibody from step (a); and
   (c) calculating said human acid glutathione S-transferase from said quantified amount from step (b) in said sample.

10. The method for diagnosing cancer according to claim 9, wherein said reacting step (a) further comprises the use of a first monoclonal antibody that specifically binds to human acid glutathione S-transferase and a second monoclonal antibody that specifically binds to human acid glutathione S-transferase, wherein said first monoclonal antibody is bound to a support and said second monoclonal antibody is labelled.

11. The method for diagnosing cancer according to claim 10, wherein said second monoclonal antibody is labeled using a member selected from the group consisting of enzymes, fluorescent substances, luminous substances, and radioactive substances.

12. A reagent kit for diagnosing cancer which is accompanied by the presence of acid glutathione S-transferase in blood comprising:
   (1) a first monoclonal antibody that specifically binds to human acid glutathione S-transferase bound to a support,
   (2) a second monoclonal antibody that specifically binds to human acid glutathione S-transferase that binds to an epitope different from the first monoclonal antibody, where said second monoclonal antibody is labelled, and
   (3) reagents for detecting said second antibody.

* * * * *